(12) United States Patent
Aberg et al.

(10) Patent No.: US 11,197,851 B2
(45) Date of Patent: Dec. 14, 2021

(54) METHODS OF TREATMENT OF ASTHMA AND COPD

(71) Applicant: Bridge Pharma, Inc., Sarasota, FL (US)

(72) Inventors: A. K. Gunnar Aberg, Sarasota, FL (US); Vincent B. Ciofalo, Branford, CT (US); Kresimir Pucaj, Zagreb (HR)

(73) Assignee: BRIDGE PHARMA INC., Sarasota, FL (US)

( * ) Notice: Subject to any disclaimer, the term of this patent is extended or adjusted under 35 U.S.C. 154(b) by 0 days.

(21) Appl. No.: 17/177,888

(22) Filed: Feb. 17, 2021

(65) Prior Publication Data

US 2021/0186945 A1    Jun. 24, 2021

Related U.S. Application Data

(63) Continuation of application No. 16/943,426, filed on Jul. 30, 2020, now Pat. No. 10,959,992, which is a continuation-in-part of application No. 16/751,539, filed on Jan. 24, 2020, now abandoned.

(60) Provisional application No. 62/809,212, filed on Feb. 22, 2019.

(51) Int. Cl.
| | |
|---|---|
| *A61K 31/4465* | (2006.01) |
| *A61K 9/00* | (2006.01) |
| *A61P 11/06* | (2006.01) |
| *A61K 45/06* | (2006.01) |

(52) U.S. Cl.
CPC ........ *A61K 31/4465* (2013.01); *A61K 9/0053* (2013.01); *A61K 9/0075* (2013.01); *A61P 11/06* (2018.01); *A61K 45/06* (2013.01)

(58) Field of Classification Search
CPC .............. A61K 31/4465; A61K 9/0053; A61K 9/0075; A61K 45/06; A61P 11/06
USPC ....................................................... 514/324
See application file for complete search history.

(56) References Cited

U.S. PATENT DOCUMENTS

| | | |
|---|---|---|
| 3,682,930 A | 8/1972 | Bourquin et al. |
| 6,297,683 B1 | 10/2001 | Drapkin et al. |
| 7,226,934 B1 | 6/2007 | Aberg et al. |
| 7,557,128 B2 | 7/2009 | Aberg et al. |
| 8,557,846 B1 | 10/2013 | Aberg et al. |
| 9,138,431 B2 | 9/2015 | Aberg et al. |
| 9,345,697 B2 | 5/2016 | Aberg et al. |
| 10,160,796 B2 | 12/2018 | Hyde-Deruyscher et al. |
| 10,494,420 B2 | 12/2019 | Hyde-Deruyscher et al. |
| 10,501,527 B2 | 12/2019 | Hyde-Deruyscher et al. |
| 2007/0191726 A1 | 8/2007 | Harnoncourt et al. |
| 2009/0054374 A1 | 2/2009 | Kennedy |
| 2010/0166804 A1 | 7/2010 | Penn |
| 2013/0045921 A1 | 2/2013 | Endo |
| 2015/0272941 A1 | 10/2015 | Aberg et al. |
| 2018/0072796 A1 | 3/2018 | Hyde-Deruyscher et al. |
| 2020/0268734 A1 | 8/2020 | Aberg et al. |

FOREIGN PATENT DOCUMENTS

| | | |
|---|---|---|
| WO | 2012108635 A2 | 8/2012 |
| WO | 2017108065 A1 | 6/2017 |
| WO | 2020172047 A1 | 8/2020 |

OTHER PUBLICATIONS

Aronson, J.K.; "Ketotifen" in Meyler's Side Effects of Drugs (16th Ed.) The International Encyclopedia of Adverse Drug Reactions and Interactions; 2016; pp. 434-435.
Asano et al.; "Allergic bronchopulmonary mycosis—pathophysiology, histology, diagnosis, and treatment"; Asia Pacific Allergy, vol. 8, Issue 3; Jul. 16, 2018; 14 pages.
Babu et al.; "Umeclidinium in chronic obstructive pulmonary disease: latest evidence and place in therapy" Therapeutic Advances in Chronic Disease, vol. 8, Issue No. 4-5; 2017; pp. 81-91.
Barnes, P.; "Inhaled Corticosteroids"; Pharmaceuticals, vol. 3, Issue No. 3; 2010; pp. 514-540; doi:10.3390/ph3030514.
Bhatty, S.; "Chronic Obstructive Pulmonary Disease (COPD) and Acute Exacerbations"; Infectious Disease Advisor; Retrieved online at https://www.infectiousdiseaseadvisor.com/home/decision-support-in-medicine/infectious-diseases/chronic-obstructive-pulmonary-disease-copd-and-acute-exacerbations/; Retrieved on Dec. 6, 2020; 10 pages.
Bist et al.; "Primary Atrophic Rhinitis: A Clinical Profile, Microbiological and Radiological Study"; ISRN Otolaryngology, vol. 2012, Article ID 404075; Oct. 7, 2012; 6 pages.
Borghardt et al.; "Inhaled Therapy in Respiratory Disease: The Complex Interplay of Pulmonary Kinetic Processes"; Canadian Respiratory Journal, vol. 2018, Article ID 2732017; Jun. 19, 2018; 11 pages.
Brode et al.; "The risk of mycobacterial infections associated with inhaled corticosteroid use"; The European Respiratory Journal, vol. 50, Issue No. 3; DOI: 10.1183/13993003.00037-2017; 2017; 10 pages.
Dietrich et al.; "Hypersensitivity in Mice: Induction of Contact Sensitivity to Oxazolone and Inhibition by Various Chemical Compounds"; International Archives of Allergy and Applied Immunology, vol. 38; 1970; pp. 246-259.
Ellis et al.; "Nonallergic rhinitis with eosinophilia syndrome"; Current Allergy and Asthma Reports, vol. 6, Issue 3; May 2006; pp. 215-220.
Evans et al.; "Inhibition of contact sensitivity in the mouse by topical application of corticosteroids"; British Journal of Pharmacology, vol. 43, Issue No. 2; 1971; pp. 403-408.
FDA News Contributors; "FDA approves first digital inhaler for asthma, COPD"; FDA News; 2019; 2 pages.

(Continued)

*Primary Examiner* — Taylor V Oh
(74) *Attorney, Agent, or Firm* — Cantor Colburn LLP

(57) ABSTRACT

Described herein are methods of administering the non-steroidal anti-inflammatory drug norketotifen, an isomer, an isomeric mixture, a prodrug, or a pharmaceutically acceptable salt thereof for the treatment of a respiratory disorders such as COPD and asthma to human patient in need of such treatment, without exposing said patient to adverse immune-suppressive effects. Methods include treating acute and potentially life-threatening exacerbations of COPD and asthma with norketotifen.

10 Claims, No Drawings

(56) References Cited

OTHER PUBLICATIONS

Fitzgerald, J. et al.; "Doubling the dose of budenoside versus maintenance treatment in asthma exacerbations" Thorax, vol. 59, Issue No. 7; 2004; pp. 550-556.
Hoye et al.; "Solubility of solid solutes in HFA-134a with a correlation to physico-chemical properties"; Journal of Pharmaceutical Sciences, vol. 97, Issue No. 1; 2008; pp. 198-208.
Hunter, et al.; "Steroid Treatment—Effects in Dogs"; VCA Hospitals website [Internet]; Retrieved Jul. 28, 2020; https://vcahospitals.com/know-your-pet/steroid-treatment-long-term-effects-in-dogs; 5 pages.
International Search Report and Written Opinion for International Application PCT/US2020/044167; International Filing Date: Jul. 30, 2020; dated Nov. 9, 2020; 12 pages.
International Search Report and Written Opinion for International Application PCT/US2020/18205 International Filing Date: Feb. 14, 2020; dated Apr. 22, 2020; 15 pages.
Kempsford et al.; "Vilanterol trifenatate, a novel inhaled long-acting beta2 adrenoceptor agonist, is well tolerated in healthy subjects and demonstrates prolonged bronchodilation in subjects with asthma and COPD"; Pulmonary Pharmacology & Therapeutics, vol. 26, Issue No. 2; 2013 pp. 256-264.
Kim et al.; "Non-steroidal anti-inflammatory drugs for the common cold"; Cochrane Database of Systematic Reviews, Issue 9, Article CD006362; 2015.
Lane, D.; "A steroid sparing effect of ketotifen in steroid-dependent asthmatics"; Clinical Allergy, vol. 10, Issue No. 5; 1980; pp. 519-525.
Lv et al.; "Cigarette smoke promotes COPD by activating platelet-activating factor receptor and inducing neutrophil autophagic death in mice"; Oncotarget, vol. 8, No. 43; Aug. 18, 2017; pp. 74720-74735.
Murphy, T. et al.; "Moraxella catarrhalis in Chronic Obstructive Pulmonary Disease"; American Journal of Respiratory and Critical Care Medicine, vol. 172, Issue No. 2; 2005; pp. 195-199.
Myrdal et al.; "Advances in Metered Dose Inhaler Technology: Formulation and Development"; AAPS PharmSciTech, vol. 15, Issue No. 2; 2014; pp. 434-455.
Nelson et al.; "The inflammatory response in chronic bronchitis"; Seminars in Respiratory and Critical Care Medication, vol. 21, Issue 2; 2000; pp. 79-86.
Nouira et al.; "Once daily oral ofloxacin in chronic obstructive pulminary disease exacerbation requiring mechanical ventilation: a randomised placebo-controlled trial"; The Lancet, vol. 358, Issue 9298; Dec. 15, 2001; pp. 2020-2025.
O'Riordan, T.G.; "Formulations and Nebulizer Performance"; Respiratory Care, vol. 47, Issue No. 11; 2002; pp. 1305-1312.
Rabe, K. et al.; "Global Strategy for the Diagnosis, Management, and Prevention of Chronic Obstructive Pulmonary Disease"; American Journal of Respiratory and Critical Care Medicine, vol. 176, Issue No. 6; 2007; pp. 532-555.
Reimer et al.; "Management of laryngopharyngeal reflux with proton pump inhibitors"; Therapeutics and Clinical Risk Management, vol. 4, Issue No. 1; 2008; pp. 225-233.
Scarupa et al.; "Nonallergic Rhinitis, With a Focus on Vasomotor Rhinitis: Clinical Importance, Differential Diagnosis, and Effective Treatement Recommendations"; The World Allergy Organization Journal, vol. 2, Issue 3; Mar. 15, 2009; pp. 20-25.
Sethi, S.; "Infection as a comorbidity of COPD"; The European Respiratory Journal, vol. 35, Issue No. 6; 2010; pp. 1209-1215.
Settipane; "Epidemiology of Vasomotor Rhinitis" WAO Journal, vol. 2; Jun. 2009; pp. 115-118.
Shukla et al.; "An antagonist of the platelet-activating factor receptor inhibits adherence of both nontypeable Haemophilus infuenzae and Streptococcus pneumoniae to cultured human bronchial epithelial cells exposed to cigarette smoke"; International Journal of COPD, vol. 11; Jul. 25, 2016; pp. 1647-1655.
Singh et al.; "Eosinophilic inflammation in COPD: prevalence and clinical characteristics"; European Respiratory Journal, vol. 44, Issue 6; 2014; pp. 1697-1700.
Stein et al.; "Incidence of chronic laryngitis" The Annals of Otology, Rhinology and Laryngology, vol. 122, Issue 12; Dec. 2013; pp. 771-774.
Suissa et al.; "Inhaled corticosteroids in COPD and the risk of serious pneumonia"; Thorax, vol. 68, Issue 11; Aug. 25, 2013; pp. 1029-1036.
Telko et al.; "Dry Powder Inhaler Formulation"; Respiratory Care, vol. 50, Issue No. 9; 2005; pp. 1209-1227.
Toews; "Impact of bacterial infections on airway diseases"; European Respiratory Review, vol. 14, Issue 95; 2005; pp. 62-68.
Vos et al.; "Global prevalence of the 50 most common sequelae"; The Lancet; Jan. 29, 2019; pp. 73-74.
Walford et al.; "Diagnosis and management of eosinophilic asthma: a US perspective"; Journal of Asthma and Allergy, vol. 7, Issue 7; Apr. 11, 2014; pp. 53-65.
Ward, G. et al.; "Treatment of late-onset asthma with fluconazole"; The Journal of Allergy and Clinical Immunology, vol. 104, Issue No. 3, Pt. 1; 1999; pp. 541-546.
Wenzel et al.; "Acute Bronchitis"; The New England Journal of Medicine, vol. 355; 2006; pp. 2125-2130.
Wikipedia contributors; "Glycopyrronium bromide"; Wikipedia, the Free Encyclopedia; 2019; Web.
Wikipedia contributors; "IC50"; Wikipedia, the Free Encyclopedia; 2019; Web.
Wikipedia contributors; "Insufflation (medicine)"; Wikipedia, The Free Encyclopedia; Sep. 13, 2019; Web.
Wikipedia contributors; "Sinusitis"; Wikipedia, The Free Encyclopedia; Oct. 16, 2019; Web.
Wikipedia contributors; "Tiotropium bromide"; Wikipedia, the Free Encyclopedia; 2019; Web.
Yasir, M. et al.; "Corticosteroid Adverse Effects"; StatPearls [Internet], Treasure Island (FL); StatPearls Publishing 2020; 15 pages; https://www.ncbi.nlm.nih.gov/books/NBK531462/.

METHODS OF TREATMENT OF ASTHMA AND COPD

CROSS-REFERENCE TO RELATED APPLICATIONS

This application is a continuation of U.S. application Ser. No. 16/943,426 filed on Jul. 20, 2020, which is a continuation in part of U.S. application Ser. No. 16/751,539 filed Jan. 24, 2020, which claims priority to U.S. Provisional Application 62/809,212 filed on Feb. 22, 2019, which is incorporated herein by reference in its entirety.

TECHNICAL FIELD

The embodiments disclosed herein relate to methods for the treatment of asthma and COPD with norketotifen, specifically RS-norketotifen.

BACKGROUND

Pulmonary disorders such as asthma and chronic obstructive pulmonary disorder (COPD) are significant pulmonary problems in humans. Asthma is an inflammatory disease of the lungs that affects all age groups of patients and is characterized by recurrent attacks (exacerbations) of breathlessness and wheezing. The global prevalence of asthma is about 330 million patients with an annual asthma-related death rate of about 500,000 patients. Asthma-related deaths occur in connection with exacerbations of the disease. COPD is an umbrella term that is used to cover certain inflammatory lung diseases such as "emphysema" and "chronic bronchitis". The estimated global prevalence of COPD is similar to asthma with about 330 million patients worldwide. However, the annual COPD-related death rate has been estimated at 3.2 million patients. COPD-related deaths occur in connection with exacerbations of the disease.

In humans, both asthma and COPD are currently treated with inhaled anti-inflammatory corticosteroids, inhaled bronchodilators, and combinations thereof. The steroids are usually administered directly into the lungs by use of various types of inhalers. Currently, no potent inflammatory drugs are available that are free from the adverse immune-suppressive effects. Even the anti-inflammatory monoclonal antibodies potently express adverse suppression of the immune system.

What is needed for the treatment of pulmonary inflammatory conditions are non-steroidal long-acting oral anti-inflammatory drugs that do not have the adverse effects of steroids.

SUMMARY

In one aspect, a method of treating a human patient in need of treatment for asthma or COPD comprises administering orally or by oral inhalation an anti-inflammatory corticosteroid medication; discontinuing the corticosteroid medication; and administering orally or by oral inhalation to the human patient a therapeutically effective amount of the anti-inflammatory compound norketotifen, an isomer, an isomeric mixture, a prodrug, or a pharmaceutically acceptable salt thereof, wherein the norketotifen, isomer, isomeric mixture, prodrug, or pharmaceutically acceptable salt thereof reduces the immune-suppression caused by the anti-inflammatory corticosteroid medication.

A method of treating a human patient in need of treatment for an acute exacerbation of asthma or an acute exacerbation of COPD comprises orally or by oral inhalation administering to the human patient in need thereof a therapeutically effective amount of norketotifen, an isomer, an isomeric mixture, a prodrug, or a pharmaceutically acceptable salt thereof; wherein the therapeutically effective amount of norketotifen, an isomer, an isomeric mixture, a prodrug, or a pharmaceutically acceptable salt thereof provides a concentration of norketotifen in the lungs of the patient that is greater than or equal to the MIC of norketotifen for *Haemophilus* influenza, *Streptococcus pneumoniae, Moraxella catarrhalis, Staphylococcus aureus, Staphylococcus intermedius, Klebsiella pneumoniae*, a *Trichophyton* sp., or a combination thereof.

A method of treating acute exacerbations of asthma or acute exacerbations of COPD in a human patient in need of such treatment comprises orally or by oral inhalation administering to the human patient an original therapeutically effective maintenance dosage of norketotifen, an isomer, an isomeric mixture, a prodrug, or a pharmaceutically acceptable salt thereof for the treatment of chronic inflammation associated with asthma or COPD; identifying a symptom indicative of onset of acute exacerbation of asthma or acute exacerbation of COPD in the human patient, wherein the symptom is an increase in severity and/or frequency of cough, an increase in breathing difficulty, change in color and/or amount of sputum, increased fatigue, reduced oxygen levels, increased carbon dioxide levels, decreased FEV-1, fever, expression of pulmonary microbial infections or a combination thereof, wherein the symptom is novel or acutely increased in severity in the patient; administering to the patient exhibiting the symptom at least a double dosage of the original therapeutically effective maintenance dosage of the norketotifen, isomer, isomeric mixture, prodrug, or pharmaceutically acceptable salt thereof; continuing the at least double dose of the original therapeutically effective maintenance dosage of norketotifen, isomer, prodrug, or pharmaceutically acceptable salt thereof until the acute exacerbation of asthma or acute exacerbation of COPD in the human patient resolves, or continuing the at least double dose of the original therapeutically effective amount of norketotifen, isomer, prodrug, or pharmaceutically acceptable salt thereof for the duration of treatment; and optionally after resolution of the acute exacerbation of asthma or the acute exacerbation of COPD, orally or by oral inhalation administering to the human patient, a revised maintenance dose of norketotifen, an isomer, an isomeric mixture, a prodrug, or a pharmaceutically acceptable salt thereof for the continued treatment of asthma or COPD.

In yet another aspect, a method of treating COPD exacerbations in a human patient suffering from COPD comprises identifying an acute onset of a symptom of COPD in the human patient, wherein the symptom comprises cough, increased mucus, wheezing, shortness of breath, frequent respiratory infections, fatigue, or a combination thereof; identifying an episode when the symptom worsens more than day-to-day variation for a period of time that persist for several days or up to weeks; and in response to the exacerbation, orally or by oral inhalation administering to the human patient a therapeutically effective amount of norketotifen, an isomer, an isomeric mixture, a prodrug, or a pharmaceutically acceptable salt thereof.

In another aspect, a method of treating a patient suffering from a respiratory disorder, COPD or asthma, comprising orally or by oral inhalation administering to the human patient a therapeutically effective amount of norketotifen, an isomer, an isomeric mixture, a prodrug, or a pharmaceutically acceptable salt thereof, while avoiding inflicting said patients with adverse corticosteroidal side effects.

DETAILED DESCRIPTION

Described herein are studies showing that norketotifen is even more potent than the well-known steroid prednisone/prednisolone in the treatment of respiratory disorders, but importantly, norketotifen is the first potent anti-inflammatory pulmonary drug to be free from the adverse immune-suppressive effects of the steroids. Thus, norketotifen can be used as a potent anti-inflammatory drug without adverse immune-suppressant activities.

It has now also been found that norketotifen expresses anti-microbial effects against several types of bacteria, fungi and mold that commonly infect the lungs of patients suffering from pulmonary disorders such as asthma and COPD and also of patients suffering from inflammatory airways disorders. Prior to the present disclosure, it had not been shown that orally or oral-pulmonary administered norketotifen has antimicrobial pulmonary effects. As shown herein, inhaled norketotifen is undoubtedly reaching and exceeding the pulmonary concentrations needed for antimicrobial efficacy.

The methods described herein relate to methods of treating asthma and COPD by administering norketotifen, an isomer, a prodrug, or a pharmaceutically acceptable salt thereof, orally, by oral inhalation or by nasal inhalation. In an aspect, the compound is RS-norketotifen. Prior to the present disclosure, the respiratory therapeutic efficacy of norketotifen administered orally and by inhalation and had not been confirmed.

Asthma is a common long-term inflammatory disease of the airways. It is characterized by variable and recurring symptoms, reversible airflow obstruction, and easily triggered bronchospasms. Symptoms include episodes of wheezing, coughing, chest tightness, and shortness of breath. Asthma can be classified as atopic and non-atopic. The symptoms of asthma can sometimes be prevented by avoiding triggers, such as allergens and irritants and by use of inhaled anti-inflammatory drugs, such as acute anti-inflammatory drugs or long-acting drugs that prevents the inflammatory symptoms of asthma.

Chronic obstructive pulmonary disease (COPD) is characterized by obstructive inflammation causing inhibited airflow and poor breathing. The older term "chronic bronchitis" is used to define a productive and recurrent cough, while the term "emphysema" is still used and refers to the existence of air in the pulmonary tissues. In contrast to asthma, the airflow reduction does not improve much with the use of bronchodilators in COPD patients. Tobacco smoking is the primary risk factor for development of COPD.

COPD is characterized by an increase in inflammatory cytokines, such as IL-1, IL-6, IL-8, IL-12, IFN-gamma, IL-18, and TNF-alpha, which are released from pro-inflammatory cells (such as mast cells, basophils, macrophages, eosinophils). Symptoms of COPD include shortness of breath, especially during physical activities, wheezing, chest tightness, chronic cough, frequent respiratory infections, and combinations thereof. COPD patients often complain of lack of energy.

In humans, both asthma and COPD are currently treated with anti-inflammatory corticosteroids, inhaled bronchodilators and most often, combinations thereof. To decrease systemic adverse effects and to shorten the onset time of the medication, corticosteroids are administered directly to the lungs by inhalation devices, such as for example hydrofluoroalkane (HFA) inhalers, metered dose inhalers (MDI), dry powder inhalers (DPI) and nebulizers. Adverse effects from use of inhalation devices are few although thrush (an oral yeast infections) and hoarseness occur. Thrush is treated with oral antifungal medications and hoarseness is usually treated by rinsing the mouth (gargling).

An advantage of using norketotifen for the treatment of asthma and COPD is that the risk for adverse systemic immune-suppression is decreased. Unlike corticosteroids which must be dosed at the lowest dose possible, norketotifen may be used in higher oral doses than possible for steroids.

In addition, the use of norketotifen will avoid adverse systemic effects of corticosteroids such as adrenal gland atrophy; cataracts; facial hair growth; glaucoma; growth retardation in children; headache; high blood pressure; increased blood glucose and loss of diabetes control; loss of potassium; menstrual irregularity; muscle weakness; obesity; osteoporosis; puffiness of the face (moon face); slow wound healing; sodium and fluid retention causing edema and weight gain; thinning and easy bruising of the skin; ulcers in the stomach and duodenum; and others.

In the treatment of respiratory disorders, norketotifen does not cause adverse immune suppression which is contrary to the steroids. Thus, norketotifen may be used in higher doses and higher concentrations and for longer periods of time than possible for steroids.

The methods described herein relate to the treatment of asthma and COPD in human patients, by oral dosing, by oral inhalation, or by nasal inhalation of norketotifen or an isomer or a prodrug or a pharmaceutically acceptable salt thereof. In an aspect, the compound is RS-norketotifen or a salt thereof. Prior to the present disclosure, the respiratory/pulmonary therapeutic efficacy of orally administered norketotifen, for example, had not been reported. Since norketotifen is a low-toxicity drug, the oral doses of norketotifen can be high during the initial loading phase and reduced during a maintenance phase.

Of particular note, norketotifen differs from the glucocorticoids, since norketotifen, after oral administration, is rapidly absorbed and is surprisingly preferentially distributed to the lungs, where the concentration of RS-norketotifen can reach concentrations that may be 100 times higher than the plasma concentration. This finding (see Table 3) is particularly surprising since it is contrary to current teaching that pulmonary drug concentrations cannot exceed the plasma concentration.

In addition to oral administration, the RS-norketotifen can be administered to the nasal passages using nasal drops or nasal sprays or by oral inhalation devices such as for example metered dose inhalers, dry powder inhalers, HFA inhalers and nebulizers using doses needed and as often as needed by the patient and selected by his/her physician or caregiver.

As used herein, norketotifen refers to norketotifen, an isomer, a prodrug, or a pharmaceutically acceptable salt thereof. RS-norketotifen refers to racemic norketotifen. In an aspect, the compound is RS-norketotifen hydrogen fumarate.

Norketotifen is an achiral molecule, but has two atropisomers, S-norketotifen and R-norketotifen, as has previously been described by Aberg et al. in U.S. Pat. Nos. 7,226,934 and 7,557,128.

As explained in U.S. Pat. Nos. 7,226,934 and 7,557,128, norketotifen had significant sedative effects when studied in an art-accepted mouse model of sedation, and further, the sedative effects were attributed to the R-isomer. It was thus proposed that only the S-isomer could be administered without sedative side effects. It has later been found that orally administered RS-norketotifen is free from sedative side effects in dogs (U.S. Pat. No. 8,557,846) and in humans (U.S. Pat. Nos. 9,138,431 and 9,345,697). Therefore, unlike for ketotifen, no dose-limiting sedative adverse effects are expected for norketotifen, even after high oral doses of norketotifen As used herein, a single isomer has an optical purity of 90% or more; preferably 98% or better. Also as used herein, an isomeric mixture has an optical purity of 90/10 to 10/90 for the S-isomer/the R-isomer. A racemate as used herein has an optical purity of between 50/50 and 60/40 for one isomer/the other isomer.

Norketotifen can be made using methods known in the art, as described in U.S. Pat. No. 3,682,930, the disclosure of which is hereby incorporated by reference for its teaching of the synthesis of norketotifen.

Prodrugs of norketotifen include N-substituted hydroxyalkyl or carboxyalkyloxyalkyl analogs thereof. Such molecules are described in U.S. Pat. No. 6,297,683. Prodrugs of norketotifen include molecules of the formula:

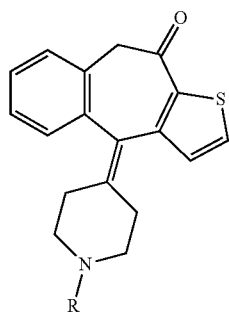

wherein R is hydroxy-$C_2$-$C_6$ alkyl or carboxy-$C_1$-$C_6$alkoxy-$C_1$-$C_6$alkyl. Additional prodrugs include substituents at the 8-position, the 10-position and/or in the 12 to 17 positions and/or inclusion of substituents on various positions on the piperidine ring.

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid as for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

Oral administration of norketotifen to treat pulmonary disorders, for approximately 1 week or less (loading dose) can then be followed by a lower maintenance dose, which at the discretion of the caregiver can be continued for 1 week, 10 days, weeks, months or years or rest of life (ROL). This is particularly important because conditions such as asthma and COPD are most often chronic conditions, requiring treatment for weeks, months, or years. Thus, norketotifen will preferably and initially be administered once or twice daily for up to one week, which is the loading dose, followed by a lower, maintenance dose of norketotifen once or twice daily or less frequently than once daily for one week, several weeks, one month, several months, one year or several years or ROL.

More specifically, in a study in dogs, (Table 2), once daily orally administered norketotifen was found to accumulate in the lungs, and the concentration in the lungs was 70 times higher than in the plasma. In a similar study in rats, the pulmonary concentration of norketotifen was 100 times higher in lungs than in plasma (Table 3). It is quite surprising that the concentration of norketotifen in the lungs is higher than the plasma drug concentration because it is generally believed in the art that pulmonary concentrations of drugs are not higher than the corresponding plasma-drug concentrations due to the lack of known transporters between the blood and the lungs.

A method of treating a human patient in need of treatment for asthma or COPD comprises administering orally or by oral inhalation an anti-inflammatory corticosteroid medication; discontinuing the corticosteroid medication; and administering orally or by oral inhalation to the human patient a therapeutically effective amount of the anti-inflammatory compound norketotifen, an isomer, an isomeric mixture, a prodrug, or a pharmaceutically acceptable salt thereof, wherein the norketotifen, isomer, isomeric mixture, prodrug, or pharmaceutically acceptable salt thereof reduces the immune-suppression caused by the anti-inflammatory corticosteroid medication.

In this aspect, the human patient has been treated with a corticosteroid, which currently is the standard of care for asthma or COPD. During the course of treatment, the corticosteroid is discontinued, and then norketotifen, an isomer, an isomeric mixture, a prodrug, or a pharmaceutically acceptable salt thereof is administered to the patient, preferably as a long-term replacement for the corticosteroid treatment.

As used herein, discontinuing can be an abrupt stop with a substantially immediate transition to norketotifen therapy. Alternatively, discontinuing can be a gradual discontinuation, over days or even weeks, wherein the dosing of the corticosteroid is gradually reduced, such as skipping doses or administering smaller doses. Replacement therapy with norketotifen can begin during the gradual discontinuation of the corticosteroid, for example such that the amount or frequency of dosing of the norketotifen is gradually increased during the discontinuation of the steroid. Alternatively, replacement therapy with the norketotifen is not started until after the last dose of the corticosteroid is administered to the patient. However the corticosteroid and norketotifen are administered, it is important that the patient receive continued anti-inflammatory drug treatment.

In an aspect, wherein the norketotifen, isomer, isomeric mixture, prodrug, or pharmaceutically acceptable salt thereof provides improved breathing and life-saving therapy to the human patient, wherein the human patient is a critically sick patient. Such therapy is particularly important for critically sick patients particularly in view of the high mortality rate for asthma and in particular for COPD patients.

In this context it is important that corticosteroids do not work well in COPD patients and in patients with severe asthma. The lack of therapeutic activity is corticosteroid resistance. High doses of corticosteroids may reduce the exacerbations by 20-25% in patients with severe disease and this is the clinical indication for their use. Except for norketotifen, effective anti-inflammatory medications for COPD-patients are not known. Also, it is difficult and currently not possible to construct a monoclonal antibody with widespread use for diseases like COPD, which are not caused by a single gene defect, but are polygenic. Due to the lack of effective medications for COPD, more than 300 million patients are without effective medication and 3.2 million COPD-patients die yearly from COPD. The following cytokines are among the multitude of cytokines involved in COPD exacerbations: IL-1, IL-6, IL-8, and TNFα; all are inhibited by norketotifen (Table 6). The simultaneous release of these cytokines in COPD exacerbations represent a pulmonary Cytokine Storm.

In another aspect, and based on current studies, the anti-inflammatory drug norketotifen, isomer, isomeric mixture, prodrug, or pharmaceutically acceptable salt thereof will prolong life compared to no treatment or to continued treatment with the corticosteroid.

In another aspect, a method of treating a human patient in need of treatment for an acute and severe exacerbation of asthma or an acute exacerbation of COPD comprises orally or by oral inhalation administering to the human patient in need thereof a therapeutically effective amount of norketotifen, an isomer, an isomeric mixture, a prodrug, or a pharmaceutically acceptable salt thereof; wherein the therapeutically effective amount of norketotifen, an isomer, an isomeric mixture, a prodrug, or a pharmaceutically acceptable salt thereof provides a concentration of norketotifen in the lungs that is greater than or equal to the MIC for *Haemophilus influenza*, *Streptococcus pneumoniae*, *Moraxella catarrhalis*, or a combination thereof. *Moraxella catarrhalis* causes 2 to 4 million exacerbation of COPD annually in the USA.

An acute exacerbation of severe asthma or an acute exacerbation of COPD is a flare-up of asthma or COPD, generally caused by a cytokine storm characterized by simultaneous release of high concentrations of numerous pro-inflammatory cytokines, resulting in worsening of the pulmonary inflammation and an increase in the intensity of symptoms. Acute COPD exacerbations are most often cause by pulmonary bacterial infections which result in simultaneous release of additional cytokines. Often, the patient will have an infection-related fever in addition the COPD symptoms.

A severe exacerbation of COPD generally results in hospitalization and patients often require mechanical respiratory support. Patients with severe acute exacerbations COPD have a significant in-hospital mortality rate which in one study was a one-year mortality of 59 percent. Without being held to theory, it is believed that mortality is caused by microbial infections which in turn cause a release of multiple cytokines, giving rise to severe pulmonary inflammation and severe pulmonary edema, often necessitating the use of respirators or similar devices. Patients suffering from severe COPD exacerbations feels worse when lying down and they often prefer sitting in a chair when sleeping. These patient generally have severe pulmonary infections, often expressed as colds, flu or pneumonia. The severe pulmonary infections and the severe inflammation cause lung damage that can be permanent.

In certain aspects, the norketotifen, isomer, isomeric mixture, prodrug, or pharmaceutically acceptable salt thereof provides life-saving therapy to asthma patients with severe exacerbations. In other aspects, the acute exacerbation of asthma or acute exacerbation of COPD in the human patient are not seldom severe and life-threatening.

In another aspect, the MIC for *Haemophilus* influenza was found to be about 0.25 mg/ml, the MIC for *Streptococcus pneumoniae* was 0.5 mg/ml, and the MIC for *Moraxella catarrhalis* was 0.25 mg/ml (see Table 9).

In certain aspects, the norketotifen, isomer, isomeric mixture, prodrug, or pharmaceutically acceptable salt thereof relieves one or more symptoms of asthma or COPD selected from phlegm, stabbing chest pain, shortness of breath, difficult breathing, wheezing, yellow or green colored mucus, fever, chills, throat pain, sinus drainage and congestion.

In certain aspects, the method further comprises diagnosing a respiratory infection associated with the acute exacerbation of asthma and particularly of COPD. Methods for diagnosing respiratory infections include medical imaging, spirometry, pulse oximetry, mucus culture, throat swab, complete blood count, blood culture, or a combination of the foregoing.

In another aspect, a method of treating acute exacerbations of asthma or acute exacerbations of COPD in a human patient in need of such treatment comprises orally or by oral inhalation administering to the human patient an original therapeutically effective maintenance dosage of norketotifen, an isomer, an isomeric mixture, a prodrug, or a pharmaceutically acceptable salt thereof for the treatment of chronic inflammation associated with asthma or COPD; identifying a symptom indicative of onset of acute exacerbation of asthma or acute exacerbation of COPD in the human patient, wherein the symptom is an increase in severity and/or frequency of cough, an increase in breathing difficulty, change in color and/or amount of sputum, increased fatigue, reduced oxygen levels, increased carbon dioxide levels, decreased FEV-1, fever, expression of pulmonary microbial infections or a combination thereof, wherein the symptom is novel or increased in severity in the patient; administering to the patient exhibiting the symptom at least a double dosage of the original therapeutically effective maintenance dosage of the norketotifen, isomer, isomeric mixture, prodrug, or pharmaceutically acceptable salt thereof; continuing the at least double dose of the original therapeutically effective maintenance dosage of norketotifen, isomer, prodrug, or pharmaceutically acceptable salt thereof until the acute exacerbation of asthma or acute exacerbation of COPD in a human patient resolves, or continuing the at least double dose of the original therapeutically effective amount of norketotifen, isomer, prodrug, or pharmaceutically acceptable salt thereof for the duration of the exacerbation treatment; and optionally after resolution of the acute exacerbation of asthma or the acute exacerbation of COPD, orally or by oral inhalation administering to the human patient, a revised maintenance dose of norketotifen, an isomer, an isomeric mixture, a prodrug, or a pharmaceutically acceptable salt thereof for the continued treatment of asthma or COPD.

In an aspect, the acute exacerbation of asthma or acute exacerbation of COPD is associated with a bacterial or fungal infection of the lungs in the human patient. The bacterial or fungal infection may be caused by bacteria, such as *Haemophilus* influenza, *Streptococcus pneumoniae*, *Moraxella catarrhalis*, or fungi, such as *Trichophyton* sp., or combinations thereof. Pulmonary infections may start with Enterovirus infections that are co-expressed by bacterial (such as H influenza, S pneumoniae and/or M catarrhalis) and/or fungal (such as *Trichophyton*) infections. The pulmonary bacterial and fungal infections trigger the degranulation of pro-inflammatory cells and the release large numbers of various cytokines from pro-inflammatory cells.

In one aspect, the at least a double dose of the original therapeutically effective amount of norketotifen, isomer, isomeric mixture, prodrug, or pharmaceutically acceptable salt thereof can be accompanied by administering antimicrobial drugs. Antimicrobial drugs for COPD and asthma patients will be as recommended by the hospital or the medical professionals and are often drugs like ofloxacin or related fluoroquinolones. In general, prescriptions of antibiotics to patients with obstructive pulmonary diseases often follow the local antibiotic-sparing rules in different countries and may include cephalosporines, macrolides, tetracyclins or quinolones. Examples of oral antifungal drugs are voriconazole and amphoterizine B.

In an aspect, the acute exacerbation of asthma or acute exacerbation of COPD in the human patient is severe or life-threatening.

In another aspect, a method of treating COPD exacerbations in a human patient suffering from COPD comprises identifying an acute onset of a symptoms of COPD in the human patient, wherein the symptom comprises ongoing cough, increased mucus, wheezing, shortness of breath, frequent respiratory infections, fatigue, or a combination thereof; identifying an episode when the symptom worsens more than day-to-day variation for a period of time that persist for several days or up to weeks; and in response to the exacerbation, orally or by oral inhalation administering to the human patient a therapeutically effective amount of norketotifen, an isomer, an isomeric mixture, a prodrug, or a pharmaceutically acceptable salt thereof.

In the foregoing method, the norketotifen eliminates the microorganisms that stimulate the release of cytokines from pro-inflammatory cells, further inhibiting the degranulation of pro-inflammatory granulocytes to reduce or prevent the release of cytokines associated with COPD, thereby terminating the exacerbation and make possible the return to a maintenance dosing of norketotifen to the patient.

In an aspect, the norketotifen is administered in the form of a tablet, a capsule, or a syrup. In another aspect, the method further comprises further administering a second therapeutically active agent, specifically a long-acting muscarinic antagonist (a LAMA), a long-acting beta receptor agonist (a LABA) or a combination thereof.

In an aspect, the oral daily loading dosage is from about 0.5 mg to about 50 mg once o more times daily of the norketotifen, isomer, prodrug or pharmaceutically acceptable salt thereof, calculated as norketotifen free base and administered one or more times daily. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg and up to 50 mg once or more times daily of norketotifen, isomer, prodrug or pharmaceutically acceptable salt thereof can be administered as the loading dosage.

In an aspect, the oral daily maintenance dosage is maintenance dosage is from about 0.5 mg to about 20 mg of norketotifen, isomer, prodrug or pharmaceutically acceptable salt thereof, calculated as norketotifen free base, and administered one or more times daily. For example, about 0.5, 1, 2, 3, 4, 5, 6, 7, 8, 9, 10, 11, 12, 13, 14, 15, 16, 17, 18, 19 or 20 mg and up to 50 mg once or more timed daily of norketotifen, isomer, prodrug or pharmaceutically acceptable salt thereof can be administered as the maintenance dosage.

In an aspect, the respiratory disorder for treatment with oral norketotifen is a pulmonary disorder in addition to asthma and COPD such as Chronic Respiratory Disease (CRD), Restrictive Lung Disease and Upper or Lower Respiratory tract infections.

In another aspect, the respiratory disorder for treatment with oral norketotifen is an airways disorder such as non-allergic rhinitis, vasomotor rhinitis, non-allergic rhinitis with eosinophil syndrome, chronic rhinitis, senile rhinitis, sinusitis, laryngitis, acute bronchitis, acute bronchitis with cough, chronic bronchitis, or nasopharyngitis.

In an aspect, the oral administration of norketotifen has avoided adverse effects associated with chronic administration of other potent anti-inflammatory drugs, such as corticosteroids, calcineurin inhibitors, phosphodiesterase-4 inhibitors, Janus kinase inhibitors and anti-inflammatory monoclonal antibodies, all of which cause adverse suppression of the immune system either systemically or locally at the site of application In addition to its anti-inflammatory properties, norketotifen has antimicrobial activity and is expected to inhibit the pulmonary growth of microorganisms such as fungi, specifically molds, and bacteria including *Malassezia* sp, *Trichophyton* sp., *Haemophilus* influenza, *Streptococcus intermedius, Moraxella catarrhalis, Candida albicans*, and *Staphylococcus* sp. *Staphylococcus* sp. bacterial infections of the lungs are not uncommon in human patients and a clinical study demonstrated mortality of 32 percent of these patients, despite antibiotic treatment of the pulmonary infections. Pulmonary infections with *Candida* sp are well-known and pulmonary *Malassezia* sp. infections are also well-known. Thus, the respiratory disorders treatable with norketotifen in accordance with the dosing regimens described herein can include bacterial and fungal pulmonary infections.

In another aspect, disclosed herein is a method of treating asthma or COPD in a human patient in need of such treatment, comprising administering by oral inhalation a therapeutically effective amount of norketotifen, an isomer, a prodrug or a pharmaceutically acceptable salt thereof to the patient suffering from asthma or COPD, wherein the lungs of said patient are affected by a respiratory bacterial, fungal or mold infection. In an aspect, the therapeutically effective amount of the norketotifen, isomer, prodrug or pharmaceutically acceptable salt thereof provides a pulmonary concentration that is equal to or greater than the minimum inhibitory concentration (MIC) value for the bacteria, fungus or mold. Table 6 provides exemplary MIC values.

Usually, a free pulmonary concentration of norketotifen that is equal to or greater than the minimum inhibitory concentration (MIC) value for the bacteria, fungi or mold may not be achieved by oral, e.g., systemic, administration. Only oral inhalation of norketotifen can provide concentrations of norketotifen that are high enough to kill microbes in the lungs. Administering norketotifen by oral inhalation (for example by a dry powder inhaler) can save the lives of COPD patients by elimination of the microbes that cause life-threatening pulmonary infections. In addition, norketotifen prevents inflammations that accompany the infections.

In another aspect, the therapeutically effective amount of the norketotifen, isomer, isomeric mixtures prodrug or pharmaceutically acceptable salt thereof reduces or eliminates a symptom of the respiratory bacterial, fungal or mold infection in the patient. Exemplary symptoms of respiratory infection include cough with phlegm, stabbing chest pain, shortness of breath, difficult breathing, wheezing, yellow or green colored mucus, fever, chills, throat pain, sinus drainage or congestion, headache, and combinations thereof.

Pulmonary infections can be diagnosed by listening for abnormal sounds in the lungs when a patient is breathing. In addition, X-ray and CT scans can be helpful to diagnose bacterial pneumonia in the lower respiratory tract. The respiratory infection can be diagnosed by medical imaging (chest x-ray or CT scan), spirometry, pulse oximetry, mucus culture, throat swab, complete blood count, blood culture, or a combination of the foregoing.

In an aspect, administration by inhalation is performed using a dry powder inhaler, a metered dose inhaler, an HFA inhaler, a nebulizer, or a digital inhaler.

In an aspect, the therapeutically effective amount of inhaled norketotifen, or an isomer, or a prodrug or a pharmaceutically acceptable salt thereof, for providing therapeutically effective pulmonary concentration will depend on the disease of the patient (asthma or COPD) and the severity of concomitant pulmonary microbial infections. While any suitable inhaler may be used, patients suffering from severe pulmonary infections may prefer a dry powder inhaler that can deliver from 10 µg and up to 500 µg of micronized norketotifen per actuation. The inhaled dose of norketotifen in severely sick patients may consist of up to six or more daily actuations from a high-capacity DPI device.

Because norketotifen is not a penicillin and because norketotifen accumulates in the lungs, it is expected to be effective in the treatment of infections with penicillin-resistant bacteria in the lungs. Exemplary bacteria include methicillin-resistant *Staphylococcus aureus* (MRSA), vancomycin-resistant *Enterococcus* (VRE), drug-resistant *Streptococcus pneumoniae* (DRSP) and multi-drug resistant *Mycobacterium tuberculosis* (MDR TB). It is understandable by those skilled in the art that norketotifen can be combined with other anti-microbial drugs.

In addition to inhibiting the growth of bacteria, norketotifen has been found to inhibit the growth of fungi, particularly the mold *Trichophyton* sp. such as *Trichophyton rubrum*, which can be found in the lungs of subjects with asthma and COPD. Thus, in an aspect, norketotifen can be administered by an inhaler to subjects in need of treatment for *Trichophyton* asthma or *Trichophyton* COPD. In an aspect, the subject demonstrates fungal sensitization demonstrated by an increase in serum IgE specific to *Trichophyton* sp. In an aspect, the subject demonstrates a fungal sensitization demonstrated by a positive skin test to *Trichophyton* sp. antigens. It is also expected that RS-norketotifen will be effective against pulmonary infections caused by *Alternaria* sp., *Cladosporium* sp. and *Penicillium* sp.

In another aspect, and built on the surprising and potent anti-mold activity of norketotifen (Example 6), methods of treating *Trichophyton* asthma or *Trichophyton* COPD in a patient in need of such treatment and comprising oral and/or inhaled administration to the patient in need thereof a therapeutically effective amount of racemic or isomeric norketotifen or a pharmaceutically acceptable salt thereof.

In another aspect, a method of treating airways mycosis in a patient in need of such treatment comprises administering to the patient in need thereof a therapeutically effective amount of racemic or isomeric norketotifen or a pharmaceutically acceptable salt thereof by oral and/or inhalation routes.

Norketotifen can also be used to treat subjects in need of treatment for allergic bronchopulmonary mycosis (ABPM), which develops mainly in patients with asthma via types I and III hypersensitivity reactions to filamentous fungi. *Aspergillus* spp., especially *Aspergillus fumigatus*, is the major causative fungus. *Aspergillus fumigatus* is typically found in the soil, however, in certain people, the immune system reacts to *Aspergillus fumigatus* antigens in the lungs. In an aspect, the subject expresses fungal sensitization demonstrated by an increase in total serum IgE and/or, the presence of IgE and IgG antibodies specific to causative fungi such as *Aspergillus fumigatus*. In another aspect, the subject demonstrates fungal sensitization demonstrated by a positive skin test to fungal antigens.

The inventors have also unexpectedly found that norketotifen inhibits muscarinic M-3 receptors. Inhibitors of muscarinic M-3 receptors inhibit constriction of bronchi and bronchioles, which may become important in the treatment of asthma and emphysema, a form of COPD.

New drugs for COPD, such as Trelega Ellipta®, GSK, contain a steroidal anti-inflammatory (such as fluticasone) and a LABA (long-acting beta receptor agonist, such as vilanterol) and a LAMA (long-acting muscarinic antagonist), such as umeclidine, glycopyrrolate, or tiotropium.

A LABA may also be added to the combination therapy of NK for selected patients with severe bronchospasms. An example of a LABA to be added is vilanterol, formoterol or RR-formoterol In another aspect, a method of treating an airways disorder in a human patient in need of such treatment comprises administering to the nasal passages of the human patient in need thereof a therapeutically effective amount of norketotifen, an isomer, an isomeric mixture, a prodrug or a pharmaceutically acceptable salt thereof to reduce a symptom of the airways disorder, wherein the airways disorder is non-allergic rhinitis, vasomotor rhinitis, nonallergic rhinitis with eosinophilia, chronic rhinitis, laryngitis, sinusitis, or nasopharyngitis.

Exemplary symptoms of non-allergic rhinitis, vasomotor rhinitis, nonallergic rhinitis with eosinophilia, chronic rhinitis, sinusitis, or nasopharyngitis include inflammation of the nasal membranes with nasal congestion, rhinorrhea, itching, sneezing, purulence, increased body temperature and/or nasal bleeding, and combinations thereof.

In an aspect, administration to the nasal passages comprises nasal insufflation, nasal inhalation or administration by nose drops.

In an aspect, the therapeutically effective amount of norketotifen, isomer, prodrug or pharmaceutically acceptable salt thereof for administration for relief of the symptoms is about 10 µg to about 1 mg per actuation, calculated as norketotifen free base.

In an aspect, a method of treating respiratory disorder in a human patient in need of such treatment comprises orally administering to the human patient in need thereof a therapeutically effective amount of norketotifen and administering a bronchodilating adrenergic beta-2 receptor agonist such as formoterol or RR-formoterol. Formoterol or RR-formoterol, for example, can be administered by inhalation. In an aspect, the norketotifen and the bronchodilating adrenergic beta-2 receptor agonist are the only drugs administered to the subject to treat the respiratory disorder. Exemplary doses are as described above.

In another aspect, a method of treating a respiratory disorder in a human patient in need of such treatment comprises orally administering to the human patient in need thereof an anti-inflammatory effective amount of norketotifen, wherein the norketotifen is the only anti-inflammatory agent administered to the subject to treat the respiratory disorder. Exemplary doses are as described above.

The embodiments disclosed herein also provide pharmaceutical compositions, which comprise norketotifen, formulated together with one or more pharmaceutically acceptable carriers.

Pharmaceutical compositions for oral administration of solid dosage forms include capsules, tablets and liquid dosage forms. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example alginates, carboxymethylcellulose, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents. Solid forms of capsules, granules, pills, and tablets can have coatings and/or shells (such as for example enteric coatings) known in the art. The compositions may also be designed to release the active ingredient(s) in a certain part of the gastrointestinal tract or in a controlled release, slow-release or in a delayed-release manner. The active compound(s) can also be microencapsulated with one or more of the above-mentioned excipients or other suitable excipients.

Liquid dosage forms for oral administration of norketotifen include pharmaceutically acceptable emulsions, solutions, suspensions, syrups and elixirs. The liquid dosage form may also contain commonly known diluents (such as for example water, other solvents, solubilizing agents), emulsifiers, such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.

Intravenous and parenteral dosage forms for administration of norketotifen are also contemplated herein. Such dosage forms may be particularly useful for administration in emergency situations such as in emergency departments and urgent care centers.

The actual dosage levels of active ingredients in the pharmaceutical compositions disclosed herein may be varied so as to obtain the desired therapeutic effect. Thus, the amount of drug used varies and will depend on factors such as the administration form, the severity of the disease, the frequency of dosing, and other circumstances (such as general health, body weight, age, etc.) known to the patient, the caretaker of the patient and/or the caring physician.

The therapeutically effective oral doses of norketotifen useful for treating human patients with pulmonary conditions will be determined by the caring physician and are generally 0.5 mg to 50 mg, calculated as norketotifen free base and dosed orally as the free base or as a salt, such as for example the hydrochloride or mesylate salts or the hydrogen fumarate salt, once, twice or more times daily. In one embodiment, the treatment is once daily dosing. The therapeutically effective dose may be administered less than once daily, such as for example one to six times weekly, wherein administration is over at least a one-week period, as determined by the patient, the caretaker of the patient and/or the caring physician.

While oral administration is preferred, in some aspects nasal insufflation of norketotifen may be possible.

The embodiments disclosed herein provide methods for treatment of disorders of the lungs in patients with norketotifen, while avoiding the sedating side effects of ketotifen and other benzocycloheptathiophene-related compounds, and while avoiding the adverse immune-suppressant effects of corticosteroids (see Examples 4, 5) and other potent anti-inflammatory compounds. The embodiments also provide treatment of pulmonary microbial disorders in human patients. Administering to the patient in need of such treatment, can consist of effective amounts of norketotifen free base or a pharmaceutically acceptable salt thereof, at a dosing frequency to be determined by the individual human patient, the caretaker of the patient and/or the caring physician. In one embodiment, frequency of the therapy is one or more doses/day of norketotifen during the first week/weeks of therapy and one or two daily doses during the following long-term maintenance therapy. The dosing under long-term maintenance therapy may be reduced to one single weekly dose. In one embodiment, frequency of the therapy is one or more doses/day of norketotifen during the initial loading-dose period and during the following maintenance dosing period. The dosing during the long-term maintenance therapy may be reduced to less than once daily, such as for example one single weekly dose.

In addition to the use of norketotifen as single-drug medication in human patients, embodiments disclosed herein also provide methods for co-administration of norketotifen with at least one drug of one of the following classes: bronchodilating agents, antibacterial agents, antifungal agents, antiviral agents, vitamin D or vitamin D analogs, cyclooxygenase inhibitors, leukotriene antagonists, lipoxygenase inhibitors, selective inhibitors of one or more cytokines, such as for example kinase inhibitors and immunomodulators, such as for example cyclosporine. The co-administration may be temporary or may be chronically used in the patient. Norketotifen and the co-administered drug can be administered to the patient separately or can be co-formulated with norketotifen for oral, parenteral, pulmonary or dermal administration. Thus, as an example, norketotifen can be administered orally and the co-administered drug may also be administered orally or by inhalation. Furthermore, norketotifen and the co-administered drug may not be administered simultaneously. Thus, as an example, norketotifen may be administered orally once daily, or once weekly, while a co-administered adrenergic agonist may have to be administered orally or pulmonary (by inhalation), once or more times daily.

When used for the treatment of pulmonary disorders, such as for example asthma or COPD, norketotifen can be combined with a therapeutically active dose of a bronchodilating drug and the bronchodilating drug can independently be administered by inhalation, nasal, parenteral, topical, transdermal, rectal, sublingual or oral administration. Common bronchodilating drugs are short-acting adrenergic beta-receptor agonists, long-acting adrenergic beta-receptor agonists, anticholinergic drugs and also methylxanthines, such as for example theophyllin. The adrenergic beta-receptor agonist can, but will not necessarily be, selected from the group consisting of albuterol (salbutamol), terbutaline, fenoterol, formoterol, vilanterol and salmeterol and the optically and therapeutically active isomers of adrenergic beta-receptor agonists. Examples of anticholinergic bronchodilators are tiopropium, umeclidine, glycopurrolate and ipratropium and a well-known bronchodilating methylxanthin is theophylline. Since both bronchial and pulmonary inflammations and broncoconstriction are hallmarks of asthma and COPD, it is advantageous that norketotifen is expressing both anti-inflammatory and broncho-dilating activities. In cases where additional bronchodilatation is needed, norketotifen can be supplemented with additional broncho-dilating drugs, such as an adrenergic beta-receptor agonist or an additional antimuscarinic M-3 drug.

Common bronchodilators that are currently used together with inhaled steroids are long-acting adrenergic beta-2 receptor agonists (LABAs), long-acting muscarinic M-3 antagonists (LAMAs) or combinations thereof. The two market leaders for the treatment of asthma are combinations of the anti-inflammatory corticosteroid fluticasone and the long-acting adrenergic beta-receptor agonist salmeterol (Advair®, Glaxo), and the combination of the anti-inflammatory corticosteroid budesonide and long-acting adrenergic beta-receptor agonist formoterol (Symbicort®, Astra-Zenica). LABAs and LAMAs may be combined with norketotifen.

The invention is further illustrated by the following non-limiting examples.

EXAMPLES

Example 1. Pulmonary Anti-Inflammatory Effects In Vivo after Oral or Parenteral Doses of Norketotifen The migration of eosinophils to the lungs of asthma- and COPD-patients is well known. Various pulmonary cells express adhesion molecules, to which eosinophils bind with great avidity, leading to accumulation, degranulation and release of toxic eosinophil cationic proteins (ECPs), toxic eosinophil peroxidases (EPOs) and eosinophil-derived neurotoxins, thereby causing severe inflammatory responses of the lung tissues.

Methods

Male Sprague-Dawley rats, 400-600 g, were used in these studies.

The study described here used subcutaneous administration of norketotifen and ketotifen by Alzet® osmotic pumps. The rats were administered either RS-norketotifen hydrogen fumarate (1.0 mg/kg/day) or RS-ketotifen hydrogen fumarate (1.0 mg/kg/day) or saline. After five days of sc infusions of test articles and the vehicle, the animals were injected, i.p. with 10 µg PAF (platelet aggregating factor) in 0.25% bovine serum albumin (BSA) in saline. The subcutaneous infusions of test articles or vehicle were continued for another twenty-four hours and the animals were then sacrificed by intraperitoneal injections of a barbiturate. The tracheae of the euthanized animals were exposed and cannulated and aliquots (6×10 ml) of a Tyrode solution were successively introduced into the lungs and aspirated by gentle compression of the thorax. The total recovery of lung fluid was usually above 80%. The cell suspensions were concentrated by low speed centrifugation (200 g for 10 min) and the resulting cell pellet was resuspended in 1 ml of a Tyrode solution. Total cell counts were performed after dilution in Turks fluid, fixation in methanol and Leishman staining.

The study shown here used norketotifen, ketotifen, and saline (control) after continuous dosing with Alzet® Osmotic pumps. The administration of PAF increased the pulmonary eosinophil counts to 250 percent, as shown in Table 1. Subcutaneous Alzet® dosing of ketotifen, 1 mg/kg/day for 6 days, reduced the PAF-induced eosinophilia to almost non-PAF levels and the sc dosing of norketotifen 1.0 mg/kg/day, for six days, had a supra-maximal effect, blocking the response to PAF completely and further reduced the eosinophil counts by 26% below the baseline (Control) level, as shown in Table 1.

TABLE 1

Inhibition of pulmonary eosinophil accumulation after continuous subcutaneous dosing of test articles, 1 mg/kg/day for six days

| TEST ARTICLE (1 mg/kg/day sc for 6 days) | N | PAF-induced esosinophilia (% ± SEM) |
|---|---|---|
| BSA + saline (Control) | 8 | 100 ± 9 |
| PAF + BSA + saline (Control) | 8 | 250 ± 4 |
| PAF + BSA + Ketotifen HF | 8 | 110 ± 3 |
| PAF + BSA + Norketotifen HF | 10 | 74 ± 4 |

BSA = bovine serum albumin;
PAF = platelet aggregating factor
HF = hydrogen fumarate (salt)
BSA = Bovine Serum Albumin
PAF = platelet aggregating factor Conclusions Both ketotifen and norketotifen expressed anti-inflammatory effects by reduced PAF-induced eosinophilia. Norketotifen was significantly more potent as a PAF-inhibitor than ketotifen. Thus, after subcutaneous dosing of the test articles (Table 1), norketotifen completely inhibited all the effects of PAF and further reduced the eosinophil counts to a level that was 26 percent below the saline control level.

In a follow-up study, it was found that the plasma concentrations of norketotifen in this study were very low: 4.0±0.24 ng/ml after sc infusion of RS-norketotifen for 5 days, indicating a surprisingly high potency of norketotifen as an anti-inflammatory drug and against pulmonary PAF-induced eosinophilia.

Most of the activity of ketotifen in this study is believed to be due to the activity of norketotifen since ketotifen is readily metabolized to norketotifen in rodents.

As known by those skilled in pharmacology, an oral dose of 1 mg/kg to rats corresponds to a Human Equivalent Dose (HED) of 0.16 mg/kg or a total human dose of approximately 1 mg to a human, weighing 60 kilograms. Similarly, an oral dose of 3 mg/kg to rats, corresponds to a total dose of approximately 3 mg to a human, weighing 60 kg.

Based on the results from this and similar studies and the important roles played by eosinophils in asthma and COPD and other respiratory diseases, it was concluded that norketotifen will be particularly effective as treatment for severe eosinophilic inflammatory diseases, such as eosinophilic asthma, eosinophilic COPD and non-allergic rhinitis with eosinophilia.

Example 2. Lung/Plasma Distribution of Norketotifen (NK) in Dogs

Purpose

To determine concentrations of NK in lungs and plasma after oral dosing of NK to beagle dogs.

Methods

One group (N=3) of female Beagle dogs (8 to 10 kg/24 to 28 months) were administered racemic norketotifen hydrogen fumarate (RS-NK-HF) 11.46 mg/kg/day for 4 consecutive days. (11.46 mg of NK-HF is equal to 8.0 mg of the free base (RS-NK-FB).

Plasma samples were collected daily on Days 2, 3 and 4. The last blood samples were taken four hours after dosing on Day 4. Lung and plasma concentrations of norketotifen were determined using a qualified LC-MS-MS analytical method. LLQ was <0.5 ng/ml. Immediately after blood collection on Day 4, all animals were euthanized with an overdose of pentobarbital, administered intravenously, followed by exsanguination. Lung tissue samples (approximately 1 g each) were collected from each animal from the left and right pulmonary lobes, samples were trimmed and dried of any access blood using absorbent paper, weighed and then kept in conical tubes frozen on dry ice and stored at −80° C. pending analysis. Six samples from each animal (3 samples per side) were analyzed. The data is shown in Table 2.

TABLE 2

Day 4 Plasma and Lung Concentrations of NK in dogs at 2 hours after oral doses, corresponding to 8.0 mg/kg/day of NK-FB for four days

| Animal Number | Day | Post-dose Lung Concentration (ng/g) | Post-dose Plasma Concentration (ng/mL) | Lung/Plasma Ratio in Dogs |
|---|---|---|---|---|
| 001 | 4 | 23590 | 301 | 78.4 |
| 002 | 4 | 79546 | 1651 | 48.2 |
| 003 | 4 | 61093 | 733 | 83.3 |
|  |  | Mean ± SEM |  | 70.0 ± 11.0 |

Conclusions

The results from this study in three dogs demonstrated that the concentration of norketotifen was on an average 70 times higher in the lungs of the dogs than in the plasma of the dogs.

Example 3. Lung/Plasma Distribution of Norketotifen in Rats

Purpose

Due to the surprising results from the Example 2 study in dogs, the decision was made to repeat the Example 2 study using a different species and more power.

Methods

Groups of male SPD rats (200-230 g) were administered racemic norketotifen hydrogen Fumarate 20 mg/kg/day (=14.4 mg/kg/day of the free base) for 10 consecutive days. Lung and plasma samples were collected and prepared and the concentrations of RS-norketotifen were determined using a qualified LC-MS-MS analytical method. LLQ (Lowest Level of Quantification) was <0.5 ng/ml. The results are provided in Table 3.

TABLE 3

Concentrations of NK free in lungs and plasma of rats during and after once daily oral doses of NK-FB, corresponding to 14.4 mg/kg free base for 10 days

| Study Day | Lung Concentration (ng/g) | Plasma Concentration (ng/mL) | Lung/Plasma Ratio in Rats |
|---|---|---|---|
| Dose Day 4 | 23612 | 178 | 133 |
| Dose Day 7 | 25355 | 276 | 92 |

TABLE 3-continued

Concentrations of NK free in lungs and plasma of rats during and after once daily oral doses of NK-FB, corresponding to 14.4 mg/kg free base for 10 days

| Study Day | Lung Concentration (ng/g) | Plasma Concentration (ng/mL) | Lung/Plasma Ratio in Rats |
|---|---|---|---|
| Last dose. Day 10 | 18171 | 229 | 79 |
| Last dose + 24 hrs | 890 | 8.3 | 107 |
|  | Mean ± SEM |  | 103 ± 11.6 |

Conclusion

There was a significant accumulation of norketotifen in lungs of rats with about 100 times (103 times) higher concentration of norketotifen in lungs than in plasma. The results from this study confirm the surprising results from the Example 2 study.

The high dose of norketotifen used in the Example 3 study was selected to correspond to the use of a once-a-day loading dose of norketotifen for 10 days. The accumulation of norketotifen in the lungs is surprising and there is no known explanation for pulmonary accumulation that can be applied to the present results.

It was concluded that the results from the drug distribution studies in dogs and rats indicate that oral administration of norketotifen may replace inhalation administration of steroidal drugs for patients suffering from respiratory diseases.

Example 4: Studies on Immunosuppression

Purpose

This study was performed to evaluate possible immunosuppressant activity of RS-norketotifen.

Methods

Male BALB/c mice, 20-24 grams, 7-12 weeks, were used. The sensitization dosing (Day 1) consisted of painting the ventral portion of the pre-shaved abdominal skin with 0.1 ml of 3.0% oxazolone in 70% ethanol. Test articles were administered orally in 1.0% methyl-cellulose, starting on Day 1 and continuing for 10 consecutive days. The challenge dosing consisted of the application of 0.05 ml of 3.0% oxazolone in 70% ethanol on both sides of the outer pinna of the right ear. The thickness of both ears of all animals was measured with a calliper before the challenge dose and 24 hours after the administration of the challenge dose (Day 10). The ear thickness of untreated mice was 0.19 to 0.20 mm. Oxazolone is not a pro-inflammatory compound and the results shown here demonstrate immuno-suppressive effects, not anti-inflammatory activity. The results are shown in Table 4.

TABLE 4

Immunosuppression in vivo in male BalB/c mice

| Test Article | N | Dose/day (mg/kg) | Increase in ear thickness (mm) | Increase in ear thickness (%) | Immuno-suppression (%) | Statistical significance (P-value) |
|---|---|---|---|---|---|---|
| Control | 16 | — | 0.153 | 100.0 | 0 | — |
| NK | 16 | 10.0 | 0.147 | 96.1 | 3.9 | ≥0.25 (NS) |
| NK | 16 | 30.0 | 0.140 | 91.5 | 8.5 | ≥0.25 (NS) |
| PRED | 8 | 0.3 | 0.108 | 70.6 | 29.4 | <0.02 |

TABLE 4-continued

Immunosuppression in vivo in male BalB/c mice

| Test Article | N | Dose/day (mg/kg) | Increase in ear thickness (mm) | Increase in ear thickness (%) | Immuno-suppression (%) | Statistical significance (P-value) |
|---|---|---|---|---|---|---|
| PRED | 8 | 1.0 | 0.084 | 55.0 | 45.0 | <0.0001 |
| PRED | 8 | 3.0 | 0.076 | 49.7 | 50.3 | <0.0001 |

NK = RS-norketotifen.
PRED = prednisolone.
NS = no statistical significance.
"Ear thickness" refers to the difference in ear thickness between Day 9 (before the challenge dose) and Day 10 (24 hours after the challenge dose).

Conclusions

Daily oral dosing of RS-norketotifen 10 or 30 mg/kg for 10 days to mice did not induce immuno-suppressant activity. The reference compound, prednisolone, expressed potent and dose-dependent immune suppression at doses that were 10 times lower than the concentrations of norketotifen Moreover, parameters examined during repeat-dose toxicology studies revealed no signs of immune system suppression after assessment of: (1) Hematology Indicators; (2) Clinical Chemistry Indicators; (3) Histopathology indicators; (4) Organ and Body Weight indicators.

Justification of the model: The classic oxazolone test method was used with minor modifications. This method has been used for over 40 years in numerous drug development projects. Oxazolone does not cause inflammation and the results shown here refer to immune-suppressive effects Example 5. Anti-Inflammatory Effects of Norketotifen and Prednisolone Purpose To compare anti-inflammatory effects of oral doses of norketotifen (NK) and prednisolone (PRED).

Methods

The effects of NK, PRED and the vehicle (5% PEG in water) were tested orally in CD-1 female mice. Under the test protocol, 20 µl of 1.0% croton oil in acetone was applied topically to both ears of three groups of mice, each group consisting of 6 mice. No attempt was made to remove the croton oil solution since the solvent evaporated within 30 seconds. The oral doses of NK and PRED were 10 mg/kg (10 ml/kg) bodyweight for both compounds and were administered 60 min before the croton oil applications. Vehicle-treated mice were dosed 10 ml/kg of water, containing 5% polyethylene glycol (PEG), which was also the solvent for the test articles. Ear thickness was measured with an electronic caliper and mean ear thickness (N=12; right+left ears) were calculated and compared with the thickness of ears from vehicle-treated mice (Student's t-test). As shown in Table 5, NK, but not PRED, expressed statistically significant anti-inflammatory effects after oral dosing.

TABLE 5

Effects of single-dose NK and single-dose PRED on croton oil-induced ear swelling

| Time after croton oil, min | Average ear thickness | | |
|---|---|---|---|
| | Vehicle | NK | PRED |
| 0 (predose) | 0.21 ± 0.02 | 0.21 ± 0.02 | 0.22 ± 0.01 |
| 90 | 0.29 ± 0.04 | 0.24 ± 0.02 *** | 0.28 ± 0.01 |
| 120 | 0.28 ± 0.02 | 0.25 ± 0.02 *** | 0.27 ± 0.01 |

N = 12 ears/group.
NK = norketotifen
PRED = prednisolone

Conclusions

NK expressed statistically significant anti-inflammatory effects when compared with the vehicle control group. Prednisolone did not express statistically significant anti-inflammatory effect in this study, probably due to less anti-inflammatory potency than norketotifen.

Example 6. Antimicrobial Activity of Norketotifen

Microorganisms such as the fungi *Aspergillus fumigatus*, *Malassezia globosa* and *Candida albicans*, the molds *Tricophyton rubrum* and *Trichophyton interdigitale* and the bacteria *Staphylococcus aureus, Staphylococcus intermedius, Klebsiella pneumoniae, Haemophilus* influenza and *Streptococcus pneumoniae* grow in human lungs, particularly in immune-compromised patients in whom the growth of such microorganisms in the lungs is enhanced by steroids and other immune-suppressive drugs.

Purpose

The current studies were designed to study antimicrobial activities of norketotifen (NK) against selected toxic microbes that are commonly found in the lungs of immune-compromised patients.

Methods

Samples of NK were challenged with between $1.0 \times 10^5$ to $1.0 \times 10^6$ cfu/ml of microorganisms. The organisms were inoculated in centrifuge tubes containing 10 mL of NK solutions and 1.0 mL samples were aliquoted from each centrifuge tube weekly. The logarithmic reductions of microorganism concentrations were determined by the plate count method by diluting in DEB (D/E neutralizing Broth) from $10^{-1}$ to $10^{-4}$ for fungi, mold and bacteria. Bacterial plates were poured with SCDA (Soybean Casein Digest Agar) and incubated at 32.5±2.5° C. for 3-5 days. —The water solubility of NK about 2% (20 mg/ml). As shown in Table 6, the MICs (Minimum Inhibitory Concentrations) for NK were read from the plates.

TABLE 6

Antimicrobial effects of NK -- MIC-values (mg/ml for norketotifen)

| | Fungi: MIC | | | Mold: MIC | | Bacteria MIC | | | | | | |
|---|---|---|---|---|---|---|---|---|---|---|---|---|
| | Af | Mp | Ca | Tr | Ti | Sa | MRSA | Si | Kp | Hi | Sp | Mc |
| NK (mg/mL) | 4.0 | 1.0 | 1.0 | 0.5 | 0.5 | 0.5 | 2.0 | 0.25 | 0.5 | 0.25 | 0.5 | 0.25 |

Fungi: Af = *Aspergillus fumigatus*. Mp = *Malassezia pachydermatis*. Ca = *Candida albicans*
Mold: Tr = *Trichophyton rubrum*. Ti = *Trichophyton interdigitale*.
Bacteria: Sa = *Staphylococcus aureus*. MRSA = Methicillin-resistant *S. aureus*. Si = *Staphylococcus intermedius*. Kp = *Klebsiella pnemoniae*. Hi = *Haemophilus influenza*. Sp = *Streptococcus pneumoniae*, Mc = *Moraxella catarrhalis*.
MIC refers to lethal concentrations of NK. Those skilled in microbiology realize that static concentrations, such as bacteriostatic and fungistatic concentrations of NK are lower than the lethal (MIC) concentrations.

The MIC-concentrations for norketotifen shown in Table 6 are high and may not be reached after oral administration of norketotifen to human patients but said MIC concentrations will be reached after inhalation, particularly if dry powder inhalers are used. These concentrations of norketotifen will be reached in the lungs only after administered of norketotifen to the patient by use of inhalation devices, such as for example dry powder inhalers (DPI).

Microbial infections play an important role as aeliologic factors in COPD. Thus, it has been established that bacteria cause up to 50 percent of acute exacerbations in COPD-patients. Bacteria also play a major role in asthma exacerbations. Chronic microbial persistence in lungs and airways is not innocuous, but cause progression of pulmonary inflammation and airways obstruction in asthma patients.

Example 7. Effects of Norketotifen on Muscarinic M-3 Receptor Binding

Purpose

The purpose of this study was to test NK in a muscarinic M-3 receptor binding assay.

Background

It is known to those skilled in the art that acetylcholine is binding to smooth muscle muscarinic receptors. Binding of acetylcholine to muscarinic M-3 receptors in the airways is causing airways constriction and inhibition of the muscarinic receptors will cause bronchial smooth muscle dilatation.

Methods

The current study used human M-3 (hM3) receptor and NK hydrogen fumarate was the antagonist in the current studies. The study used NK in duplicates at five dose-levels from 1.0E-08M to 1.0E-04M.

Results

As calculated from the mean values Ki (M) was calculated to be 2.2E-06M of norketotifen free base.

Conclusions

The pulmonary distribution of NK in humans is not known. It may become advantageous to co-administer norketotifen with bronchodilators, such as long-acting antimuscarinic (LAMA) and/or long-acting adrenergic beta-agonistic (LABA) compounds, when NK is administered to human patients.

Example 8: Inhibition of Cytokine Release

Purpose

The objective of this study was to assess the ability of norketotifen to inhibit cytokine release from stimulated human white blood cells.

Methods

The study was conducted in two phases. The first phase included optimization of the test methodology and included also dose-range finding studies, using buffy coats from 3 human donors, stimulated with phytohemagglutinin (PHA). The concentrations of the test article and the duration of exposure were optimized to obtain acceptable dose-response ratios. Following optimization of the test conditions, a final protocol was issued. In the Main Study, buffy coats from 5 healthy human male donors were stimulated with PHA, 5 µg/ml.

The inhibitory effects of three concentrations of NK and one concentration of ketotifen were evaluated in the Main Study. The buffy coats were resuspended in assay media and were pre-incubated for 30 min with either vehicle/saline, ketotifen (10 µM) or norketotifen (1.0; 10 or 100 Following these preincubations, the white blood cell suspensions were stimulated for 16 hours with PHA, 5 µg/ml. The cell system supernatants were then harvested and stored frozen.

Results

Table 7 demonstrates a lack of inhibition by ketotifen, but dose-depending inhibitory effects of NK on the in vitro release of the pro-inflammatory cytokines. TNFα, IL-4 and IL-13.

TABLE 7

Effects of norketotifen and ketotifen on PHA-induced release of cytokines from human buffy coats. (Only pulmonary-related cytokines shown here)

| | Ketotifen (%) | Norketotifen (%) | | |
|---|---|---|---|---|
| Cytokine | 10 uM | 1 uM | 10 uM | 100 uM |
| IL-6 | 0.00 | 0.00 | 33.13[1] | 88.16[1] |
| TNF-α | 39.98 | 45.57[2] | 63.07[1] | 95.68[1] |
| IL-4 | 0.00 | 0.00 | 14.32 | 98.27[1] |
| IL-2 | 0.00 | 0.00 | 46.63[1] | 93.47[1] |
| IL-1β | 0.00 | 0.00 | 16.20 | 57.00[1] |
| IL-10 | 0.00 | 12.71[2] | 24.80[2] | 90.40[1] |
| IFN-γ | 0.00 | 0.00 | 16.54[2] | 71.56[1] |
| IL-8 | 30.73 | 10.29[2] | 34.36[1] | 78.29[1] |
| IL-13 | 0.00 | 0.00 | 34.49[1] | 74.25[1] |

Bold values marked[1] denote statistically significant difference ($p < 0.05$) when compared with vehicle.
Bold values marked[2] denote decrease in concentration that was not statistically significant.

Conclusions

NK dose-dependently inhibited the release of cytokines from human white blood cells. No statistically significant inhibition of cytokine release was expressed by ketotifen.

Footnote

The concentration of the test article had to be high in this study since the test kit used a high concentration of the agonist PHA (5 µg/ml) and a long exposure time (16 hrs).

Example 9: Exemplary Oral Dosage Formulation

To make tablets, NK is blended with lactose and cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet. Those skilled in the art realize that formulations can also be administered to the patient in the form of for example a capsule, a cream, an ointment or a liquid formulation. Both norketotifen salts and norketotifen free base can be formulated as tablets.

TABLE 8

Tablet formulations

| Ingredient | Amount per tablet | Amount per batch |
|---|---|---|
| Norketotifen (NK) | 8 mg | 800 g |
| Microcrystalline cellulose | 24 mg | 2400 g |
| Lactose | 56 mg | 5600 g |
| Calcium stearate | 1.4 mg | 140 g |
| FD&C Blue #1 Lake | 0.03 mg | 3 g |

Example 10: Inhalation Dosage Forms

In an aspect, a dosage form for inhalation is a nebulizer. Exemplary nebulizer devices include the Respimat®, Soft Mist™ Inhaler (Boehringer Ingelheim), the AERx® Pulmonary Delivery System (Aradigm Corp.), and the PARI LC Plus® Reusable Nebulizer (Pari GmbH). An exemplary composition for use in a nebulizer inhaler comprises an isotonic aqueous solution comprising from about 0.05 µg/mL to about 10 mg/mL of norketotifen. In one aspect, such a solution has a pH of about 3.5-6.

Alternatively, a composition comprising the active agent(s)/active ingredient(s) may be administered by inhalation using a dry powder inhaler (DPI). DPIs typically administer the active agent as a free-flowing powder that is dispersed in a subject's air-stream during inspiration. In order to achieve a free flowing powder, the active agent(s)/active ingredient(s) is typically formulated with a suitable excipient such as lactose, starch, mannitol, dextrose, polylactic acid, polylactide-co-glycolide, or combinations thereof. Typically, the active agent(s)/active ingredient(s) is micronized and combined with an excipient to form a blend suitable for inhalation. Accordingly, in one aspect, the active agent(s)/active ingredient(s) is in micronized form. For example, a representative composition for use in a DPI (dry powder inhaler) comprises dry lactose having a particle size between about 1 µm and about 100 µm (e.g., dry milled lactose) and micronized particles of the active agent. Such a dry powder formulation can be made, for example, by combining lactose with the active agent and then dry blending the components. Alternatively, if desired, the active agent can be formulated without an excipient. The composition is then typically loaded into a DPI, or into inhalation cartridges or capsules for use with a DPI. DPIs are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Diskus® or Accuhaler™ (GlaxoSmithKline), Easyhaler® (Orion Pharma), Eclipse® (Aventis), FlowCaps® (Hovione), HandiHaler® (Boehringer Ingelheim), Pulvinal® (Chiesi), Rotahaler® (GlaxoSmithKline), SkyeHale™ or Certihaler® (SkyePharma), Synchrobreathe Inhaler (Cipla), Twisthaler® (Schering-Plough), Turbuhaler® (AstraZeneca), Ultrahaler® (Aventis), and the like.

Alternatively, the composition comprising the active agent may be administered by inhalation using a metered-dose inhaler (MDI). Such MDIs typically discharge a measured amount of the active agent using compressed propellant gas. Metered-dose formulations thus typically comprise a solution or suspension of the active agent in a liquefied propellant, such as a chlorofluorocarbon such as $CCl_3F$ or a hydrofluoroalkane (HFA) such as 1,1,1,2-tetrafluoroethane (HFA 134a) and 1,1,1,2,3,3,3-heptafluoro-n-propane (HFA 227), although HFAs are generally preferred due to concerns about chlorofluorocarbons affecting the ozone layer. Additional optional components of HFA formulations include co-solvents, such as ethanol or pentane, and surfactants, such as sorbitan trioleate, oleic acid, lecithin, and glycerin. A representative composition for use in an MDI comprises from about 0.01-5 wt % of active agent; from about 0-20 wt % ethanol; and from about 0-5 wt % surfactant; with the remainder being an HFA propellant. Such compositions are typically prepared by adding a chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of the MDI. MDIs are well known to those of ordinary skill in the art, and many such devices are commercially available, with representative devices including AeroBid® Inhaler System (Forest Pharmaceuticals), Atrovent® Inhalation Aerosol (Boehringer Ingelheim), and the like. Alternatively, a suspension formulation can be prepared by spray drying a coating of surfactant on micronized particles of the active agent.

Example 11: Intranasal Dosage Forms

Intranasal dosage forms can be formulated in an aerosol form, spray, mist or in the form of drops. Intranasal compositions can include a mucoadhesive agent, a solubilizer, a preservative, a flavoring agent, a vehicle, and combinations thereof.

Examples of mucoadhesive agent include, but are not limited to polyacrylic polymers like carbopols, polycarbophil, carboxymethylcellulose or its pharmaceutically acceptable salt, microcrystalline cellulose, hydroxyethylcellulose, hydroxypropyl cellulose, hydroxypropylmethyl cellulose (i.e., hypromellose), methylcellulose, poloxamers, pectin, xanthan gums, alginates, gelatin alone or in any combination thereof. Nasal compositions can contain about 0.05 to about 5% w/v of a mucoadhesive agent.

Examples of solubilizers (or crystal growth inhibitors) include, but are not limited to d-alpha tocopheryl polyethylene glycol 1000 succinate (Vitamin E TPGS), macrogol (15)-hydroxystearate (Solutol HS 15), polyoxyethylene-polyoxypropylene copolymer (Poloxamer, Pluronic, such as poloxamer 188), PEO-PLLA diblock copolymer, PEG-PLGA-PEG triblock, copolymer, cyclodextrins, hydroxypropyl betadex, polyoxyethylene castor oil derivatives, povidone, sulfobutylether-b-cyclodextrin, tricaprylin, triolein, glyceryl monostearate, sorbitan esters (sorbitan fatty acid esters), polyoxyethylene fatty acid esters, polysorbate 80, polysorbate 20 or macrogol-15-hydroxysterate. Nasal compositions can contain from about 0.2 to about 10.0% w/v of a solubilizer.

Examples of preservatives include benzalkonium chloride, sodium benzoate, methyl, ethyl, propyl or butyl paraben, benzyl alcohol, phenylethyl alcohol, benzethonium chloride, chlorobutanol, potassium sorbate or combination thereof. Nasal compositions can contain from about 0.01 to about 1% w/v of a preservative. Liquid compositions containing norketotifen may not need an added preservative since the antimicrobial activity of the norketotifen molecule can make the formulations self-preserving, which is advantageous since preservatives, such as benzalkonium chloride are toxic entities.

Exemplary flavoring agents include flavor anise, flavor apple, flavor apricot, flavor banana, flavor buttermint, flavor citrus, flavor orange, flavor menthol mint, flavor mint, flavor peppermint, flavor spearmint, alone or in any combinations thereof. Nasal compositions disclosed may contain from about 0.01% w/v to about 0.5% w/v of a flavoring agent.

Examples of vehicles include, but are not limited to, saline, water, dextrose or combinations thereof. The pH of compositions described herein may be about 3.0 to about 7.4 and all values in between.

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid as for the compound of the present invention include acetic, benzenesulfonic (besylate), benzoic, camphorsulfonic, citric, ethanesulfonic, fumaric, gluconic, glutamic, hydrobromic, hydrogen fumaric, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

The term "antimicrobial" as used herein refers to antibacterial, antifungal and anti-mold activities or effects.

The term "patient" as used herein refers to human patients and canine patients.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted.

As used herein, when referring to dosage amount, the term "about" includes amounts to ±10% of the recited value.

As used herein, the term "chronic administration" is defined as three or more consecutive days of administration. Acute administration of norketotifen refers to a single administration of the drug.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating acute exacerbations of asthma or acute exacerbations of chronic obstructive pulmonary disorder (COPD) in a human patient in need of such treatment comprising orally or by oral inhalation administering to the human patient an original therapeutically effective maintenance dosage of norketotifen, an isomer, an isomeric mixture, a prodrug, or a pharmaceutically acceptable salt thereof;

identifying a symptom indicative of onset of acute exacerbation of asthma or acute exacerbation of COPD in the human patient, wherein the symptom is an increase in severity and/or frequency of cough, an increase in breathing difficulty, change in color and/or amount of sputum, increased fatigue, reduced oxygen levels, increased carbon dioxide levels, decreased FEV-1, fever, expression of pulmonary microbial infections or a combination thereof, wherein the symptom is novel or acutely increased in severity in the patient;

administering to the patient exhibiting the symptom at least a double dosage of the original therapeutically effective maintenance dosage of the norketotifen, isomer, isomeric mixture, prodrug, or pharmaceutically acceptable salt thereof;

continuing the at least double dose of the original therapeutically effective maintenance dosage of norketotifen, isomer, prodrug, or pharmaceutically acceptable salt thereof until the acute exacerbation of asthma or acute exacerbation of COPD in the human patient resolves, or continuing the at least double dose of the original therapeutically effective amount of norketotifen, isomer, prodrug, or pharmaceutically acceptable salt thereof for the duration of treatment; and optionally after resolution of the acute exacerbation of asthma or the acute exacerbation of COPD, orally or by oral inhalation administering to the human patient, a revised maintenance dose of norketotifen, an isomer, an isomeric mixture, a prodrug, or a pharmaceutically acceptable salt thereof for the continued treatment of asthma or COPD, wherein the prodrug is

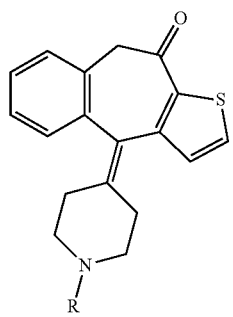

wherein R is hydroxy-C2-C6 alkyl or carboxy-C1-C6alkoxy-C1-C6alky, and wherein the norketotifen, isomer, isomeric mixture, prodrug, or pharmaceutically acceptable salt thereof is the only treatment administered to treat the acute exacerbations of asthma or acute exacerbations of COPD.

2. The method of claim 1, wherein the at least a double dose of the original therapeutically effective amount of norketotifen, isomer, prodrug, or pharmaceutically acceptable salt thereof is accompanied by administering an antimicrobial drug.

3. The method of claim 1, wherein the human patient has a bacterial or fungal infection of the lungs.

4. The method of claim 3, wherein the bacterial or fungal infection is caused by *Haemophilus* influenza, *Streptococcus pneumoniae, Moraxella catarrhalis, Staphylococcus aureus, Staphylococcus intermedius, Klebsiella pneumoniae*, a *Trichophyton* sp., or a combination thereof.

5. A method of treating chronic obstructive pulmonary disorder (COPD) exacerbations in a human patient suffering from COPD comprising identifying an acute onset of a symptom of COPD in the human patient, wherein the symptom comprises cough, increased mucus, wheezing, shortness of breath, frequent respiratory infections, fatigue, or a combination thereof;

identifying an episode when the symptom worsens more than day-to-day variation for a period of time that persist for several days or up to weeks; and in response to the exacerbation, orally or by oral inhalation administering to the human patient a therapeutically effective amount of norketotifen, an isomer, an isomeric mixture, a prodrug, or a pharmaceutically acceptable salt thereof, wherein the prodrug is

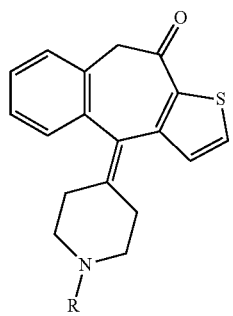

wherein R is hydroxy-C2-C6 alkyl or carboxy-C1-C6alkoxy-C1-C6alkyl, and wherein the norketotifen, isomer, isomeric mixture, prodrug, or pharmaceutically acceptable salt thereof is the only treatment administered to treat the acute exacerbations of COPD.

6. The method of claim 5, wherein the human patient has a bacterial or fungal infection of the lungs.

7. The method of claim 6, wherein the bacterial or fungal infection is caused by *Haemophilus* influenza, *Streptococcus pneumoniae, Moraxella catarrhalis, Staphylococcus aureus, Staphylococcus intermedius, Klebsiella pneumoniae*, a *Trichophyton* sp., or a combination thereof.

8. A method of treating a human patient in need of treatment for eosinophilic asthma or eosinophilic COPD, the method comprising daily orally or by inhalation administering to the human patient in need thereof a therapeutically effective amount of norketotifen, an isomer, a prodrug, or a pharmaceutically acceptable salt thereof, wherein the therapeutically effective amount of norketotifen, isomer, prodrug, or pharmaceutically acceptable salt thereof provides pulmonary accumulation of norketotifen and inhibits pulmonary eosinophil accumulation, wherein the prodrug is

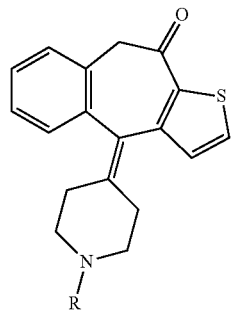

wherein R is hydroxy-C2-C6 alkyl or carboxy-C1-C6alkoxy-C1-C6alkyl.

9. The method of claim 8, wherein the therapeutically effective amount of norketotifen is 0.5 to 50 mg once or twice daily.

10. The method of claim 8, wherein the therapeutically effective amount of norketotifen is 0.16 to 0.48 mg/kg based on norketotifen hydrogen fumarate.

* * * * *